United States Patent
Maxwell et al.

(10) Patent No.: US 8,070,808 B2
(45) Date of Patent: Dec. 6, 2011

(54) VARIABLE COHESIVE GEL FORM-STABLE BREAST IMPLANT

(75) Inventors: G. Patrick Maxwell, Nashville, TN (US); Thomas E. Powell, Santa Barbara, CA (US); Daniel A. Carlisle, Santa Barbara, CA (US)

(73) Assignee: Allergan, Inc., Irvine, CA (US)

( * ) Notice: Subject to any disclaimer, the term of this patent is extended or adjusted under 35 U.S.C. 154(b) by 112 days.

(21) Appl. No.: 11/586,134

(22) Filed: Oct. 25, 2006

(65) Prior Publication Data

US 2007/0135916 A1 Jun. 14, 2007

Related U.S. Application Data

(60) Provisional application No. 60/730,559, filed on Oct. 26, 2005.

(51) Int. Cl.
*A61F 2/12* (2006.01)
(52) U.S. Cl. .................... 623/8; 623/7; 623/23.74
(58) Field of Classification Search ........... 623/8, 23.74, 623/7
See application file for complete search history.

(56) References Cited

U.S. PATENT DOCUMENTS

| | | |
|---|---|---|
| 3,681,787 A | 8/1972 | Perras |
| 5,480,430 A | 1/1996 | Carlisle |
| 5,545,217 A * | 8/1996 | Offray et al. .................... 623/8 |
| 5,824,075 A | 10/1998 | Thielbar |
| 5,902,335 A * | 5/1999 | Snyder, Jr. .................... 623/7 |
| 6,605,116 B2 | 8/2003 | Falcon |
| 6,955,690 B1 * | 10/2005 | Cao .................... 623/7 |

FOREIGN PATENT DOCUMENTS

| | | |
|---|---|---|
| DE | 296 07 969 U1 | 6/1996 |
| EP | 0178483 | 4/1986 |
| WO | WO 98/10803 A1 | 3/1998 |
| WO | WO 99/16389 A1 | 4/1999 |

* cited by examiner

*Primary Examiner* — David Isabella
*Assistant Examiner* — Yashita Sharma
(74) *Attorney, Agent, or Firm* — Linda A. Fox; Stephen Donovan; Debra Condino

(57) ABSTRACT

A variable cohesive gel form stabilizing implant is disclosed for augmentation or reconstruction of the breast. The prosthesis of this invention comprises an implantable shell or envelope (not limited to a single shell or envelope), filled with a biocompatible gel, or gels, having alterations in gel cohesiveness to maintain stable form, shape, and dimension after surgical implantation. The gel cohesiveness may increase, with increased volume or dimension of the prosthesis. The variable cohesiveness of the gel filler material may be altered by any means (i.e. chemical, fabrication, etc.). The variable cohesive gel form stabilizing implant has shape retention characteristics to maintain its form, thereby reducing or eliminating the undesirable effects of shell wrinkling, knuckling, scalloping or deformation, which can occur at the upper or lower pole of the prostheses, along the perimeter of the shell or at the base, post-implantation. Finally, the variable cohesive gel form stabilizing implant provides new control and possibilities for achieving and preserving the most natural breast shape.

8 Claims, 5 Drawing Sheets

VARIABLE COHESIVE GEL FORM-STABLE BREAST IMPLANT

CROSS REFERENCE TO RELATED APPLICATIONS

This application claims priority to U.S. Provisional Application No. 60/730,559, filed Oct. 26, 2005, which is expressly incorporated herein by reference in its entirety.

BACKGROUND OF THE INVENTION

1. Field of the Invention

The present invention relates generally to a medical prostheses and more particularly to a variable cohesive gel, form stabilizing, implant which may be used for augmentation or reconstruction of the breast. The implant may be a mammary prosthesis or a soft tissue expander.

2. Discussion of the Related Art

Today, augmentation or reconstruction of the breast requiring an implantable medical prosthesis has become fairly common practice in the art of plastic and reconstructive surgery. Typical permanent prostheses, which are often selected for these procedures, include round silicone shells, or envelopes, pre-filled with silicone gel or filled at the time of surgery with normal saline solution.

In recent years, the prostheses used for these procedures have raised cause for concern with respect to maintaining breast shape after surgical implantation. During post-operative follow-up—once healing has progressed—surgeons often observe undesirable alterations in the patient's breast shape, specifically signs of skin and/or soft tissue deformation, commonly known to those skilled in the art as prosthesis wrinkling, knuckling or scalloping. These adverse effects usually occur at the upper or lower pole of the prostheses, along the perimeter of the prosthesis shell or at the base, i.e. the inferior portion closest to the inframammary fold, and become more evident when the recipient changes her anatomical position. Moreover, with the patient in an upright position, these unstable prostheses have been known to collapse or fold in the upper pole and knuckle in the lower pole, further increasing risk of deformed breast shape. Medical prostheses have been proposed in an attempt to eliminate these clinical problems, but adverse alterations in breast shape continue to exist.

As described in U.S. Pat. No. 6,605,116, implantable mammary prostheses generally have a relatively flat posterior face that is placed against the patient's chest and a domed anterior face that projects outward. It is often desirable for the perimeter region, where the anterior face meets the posterior face, to have a relatively small radius of curvature, particularly at the upper pole or superior portion of the prosthesis, i.e., the portion of the prosthesis that is uppermost when the patient is standing. A relatively narrow radius of curvature in the transition between the anterior face and the posterior face in the upper pole of the prosthesis is desirable because it permits a relatively smooth transition between the mammary tissue and the implant when the prosthesis is implanted. But a small radius is sometimes associated with the appearance of creases that extend inward from the perimeter of the prosthesis in the region of relatively small radius. This is sometimes referred to as a scalloping effect. Scalloping tends to occur when the prosthesis is filled with fluid or gel and the patient is upright such that the weight of the filling material is pulling downward on the prosthesis. The creases often appear on the anterior face and around the perimeter of the prosthesis. This is aesthetically undesirable as the creases can sometimes be discerned through the overlying skin of the patient.

U.S. Pat. No. 5,480,430 relates to a fluid-filled breast prosthesis for surgical implantation beneath the skin having a wrinkle resistant, elastic outer shell that is adapted to resist deformation or wrinkling during movement of the fluid filler. The outer shell, or envelope, has superior and inferior portions. The wall of the superior portion of the shell is substantially thickened with respect to the wall thickness of the inferior portion of the shell. The shell forms an envelope with an inner cavity, which is filled with a biocompatible liquid such as saline. The presence of the thickened superior portion of the shell prevents wrinkles from forming in the breast prosthesis during fluid displacement, such as when the breast prosthesis recipient changes her anatomical position. The differentially thickened shell has a posterior base portion, which may be reinforced to further stabilize the prosthesis.

U.S. Patent Application No. US 2002/0143396 A1 (U.S. Pat. No. 6,605,116) relates to reinforced radius mammary prostheses and soft tissue expanders. The prosthesis is configured such that the average thickness of the shell in the region where the posterior and anterior faces meet is greater, e.g., at least twice the average thickness of the shell in the region of the anterior face. The inventors suggest this reinforcement can reduce or eliminate undesirable scalloping effects along the upper perimeter of the prosthesis that can otherwise occur when gravity pulls downward on a filled prosthesis.

Implants having fillers of varying density are also known in the art. For example, Inamed's Style 510 Dual Gel breast implant contains two different cohesive gels. The posterior of the implant is made from standard cohesive gel, while the anterior is made from a high cohesive gel. This configuration provides superior projection and support, emphasizing the nipple/areola area of the implant.

Heretofore, fillers of varying density were use only to provide anterior projection. As described herein, cohesive gel fillers of varying density, particularly around the perimeter and in the inferior and posterior regions, may be used to stabilize an implant, maintain its form and reduce or eliminate wrinkling, knuckling, scalloping or other deformation of the shell.

SUMMARY OF THE INVENTION

It is an object of this invention to provide a variable cohesive gel form-stable implant, with shape retention characteristics to maintain form, and to reduce or eliminate the undesirable effects of shell wrinkling, knuckling, scalloping or deformation that may occur at the upper or lower pole of the prostheses, along the perimeter of the shell or at the base, post-implantation.

It is another object of this invention to provide a prosthesis that will maintain its shape should the recipient change her anatomical position.

These and other objects of the invention will now become apparent as we turn to the preferred embodiments.

BRIEF DESCRIPTION OF THE DRAWINGS

The accompanying drawings which are included to provide a further understanding of the invention and are incorporated in and constitute a part of this specification, illustrate embodiments of the invention and together with the description serve to explain the principles of the invention. In the drawings, the degree of gel cohesiveness (cross-linking) is indicated by shading, i.e. darker shading indicates greater cohesiveness. In the drawings.

DETAILED DESCRIPTION OF THE PREFERRED EMBODIMENTS

Reference will now be made in detail to the preferred embodiments of the invention. This invention may, however, be embodied in many different forms and should not be construed as limited to the embodiments set forth herein. In addition, and as will be appreciated by one of skill in the art, the invention may be embodied as a method, system or process.

The implants of the present invention may be used for augmentation or reconstruction of the breast. The variable cohesive gel form stabilizing implant, with shape retention characteristics to maintain form, is characterized by alterations in gel filler cohesiveness. The variable cohesiveness of the gel filler material may be altered by any means (i.e. chemical, fabrication, etc.). It will be appreciated by those skilled in the art that manipulation of the chemical formulation of the gel may result in greater mechanical properties. For example, as more cross-links are formed, a stiffer gel results, allowing for a more form-stable implant.

It should be noted that the invention is not limited to a single shell or envelope. The prosthesis can have a single lumen or multiple lumens within its shell, although the use of cohesive gel minimizes the need for separate lumens. The invention may be employed in an implant having either a smooth or textured outer shell. The shell can be circular, oval, crescent-shaped or other suitable shapes. It can be formed of silicone rubber, a laminate of various forms of silicone, silicone copolymers, polyurethane, and various other elastomers in various combinations. The gel cohesiveness may increase with increased volume or dimension of the prosthesis.

Although examples of the invention are provided in FIGS. 1 through 5, one skilled in the art will appreciate that gel form and cohesive configuration may vary without departing from the scope of the invention.

Figure 1:
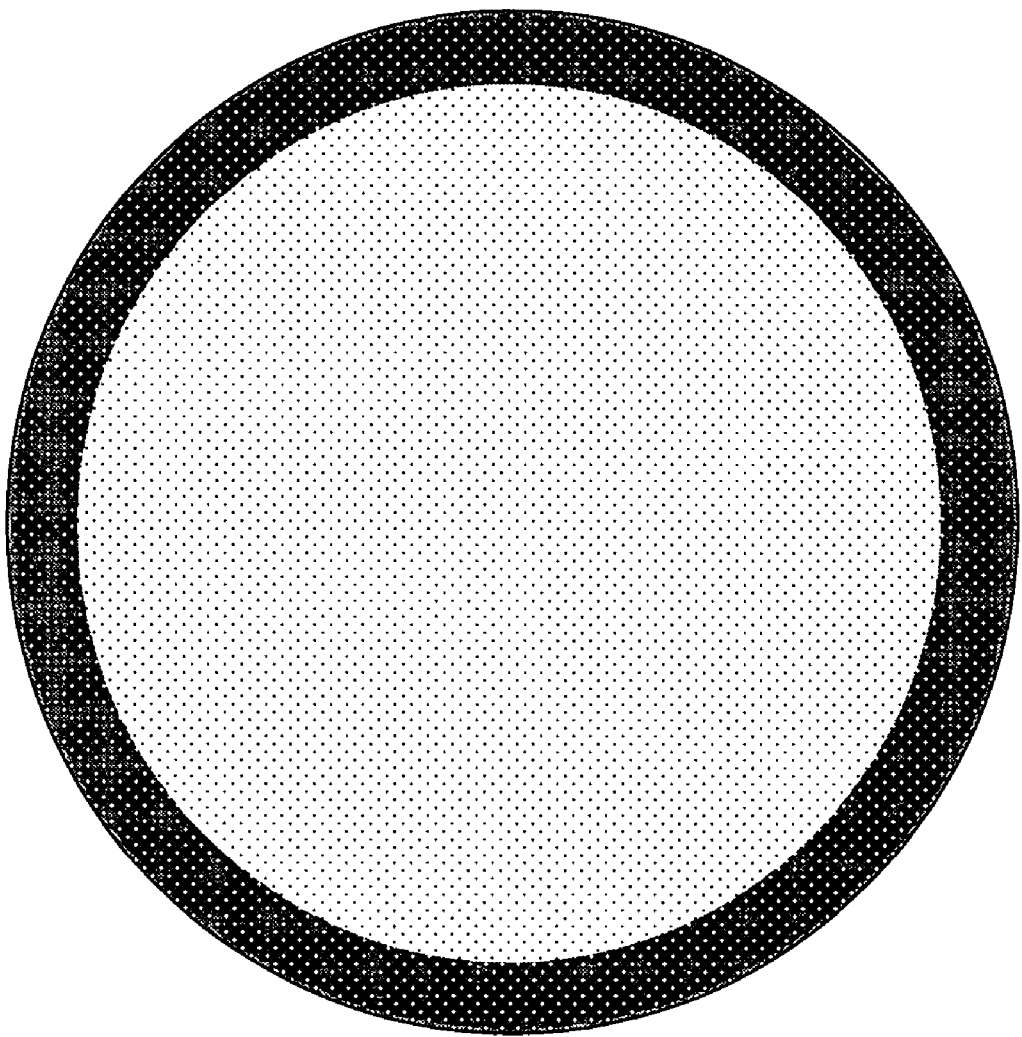
FIG. 1 is an anterior view of a round breast prosthesis made according to one aspect of to the present invention.

As illustrated in FIG. 1, one embodiment of a prosthesis of the present invention comprises a round implantable shell or envelope and a gel filler having a higher degree of cohesiveness at the perimeter or periphery of the implant.

Figure 2:
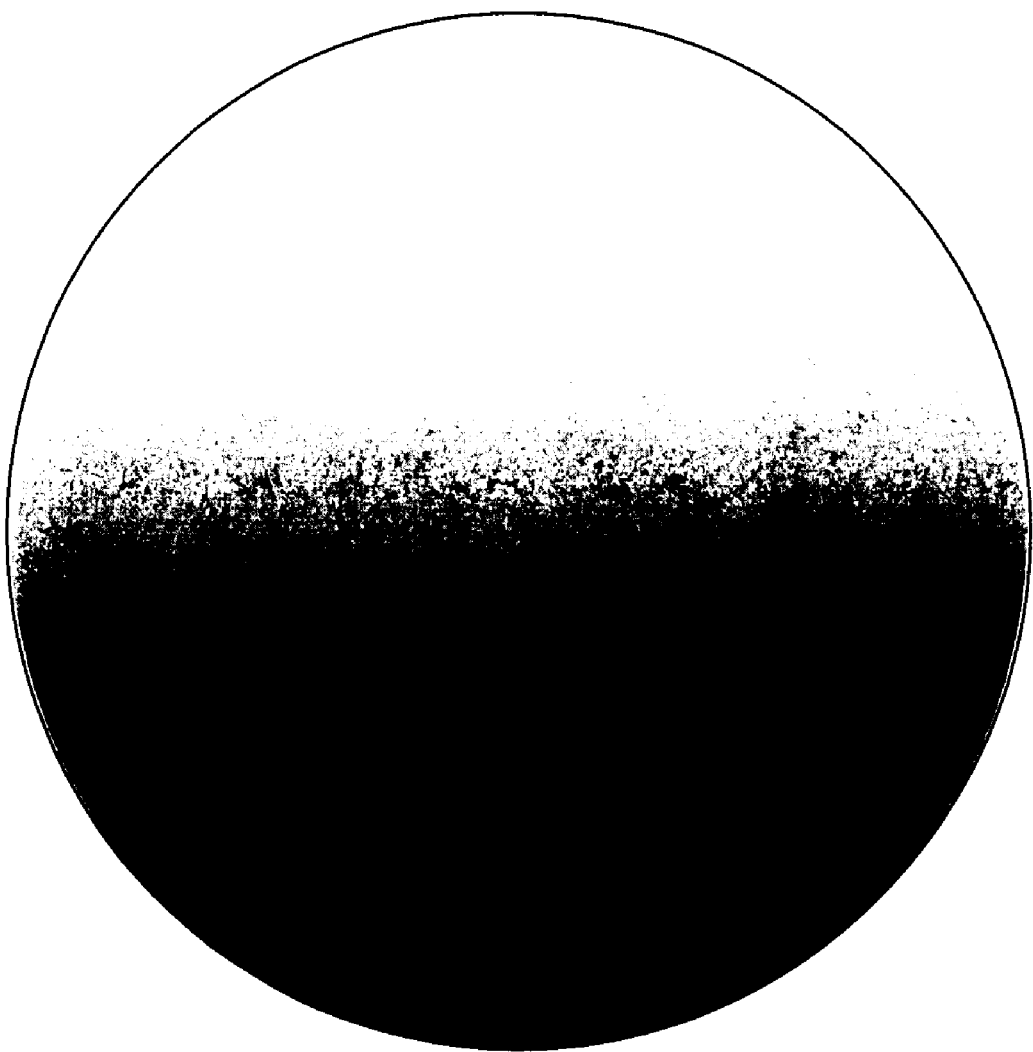
FIG. 2 is an anterior view of a round breast prosthesis made according to another aspect of the present invention.

In FIG. 2, another embodiment of a prosthesis of the present invention is shown comprising a round implantable shell or envelope and a gel filler having a greater degree of cohesiveness at the inferior portion of the implant, with a decreasing gradient towards the superior aspect of the implant.

Figure 3:
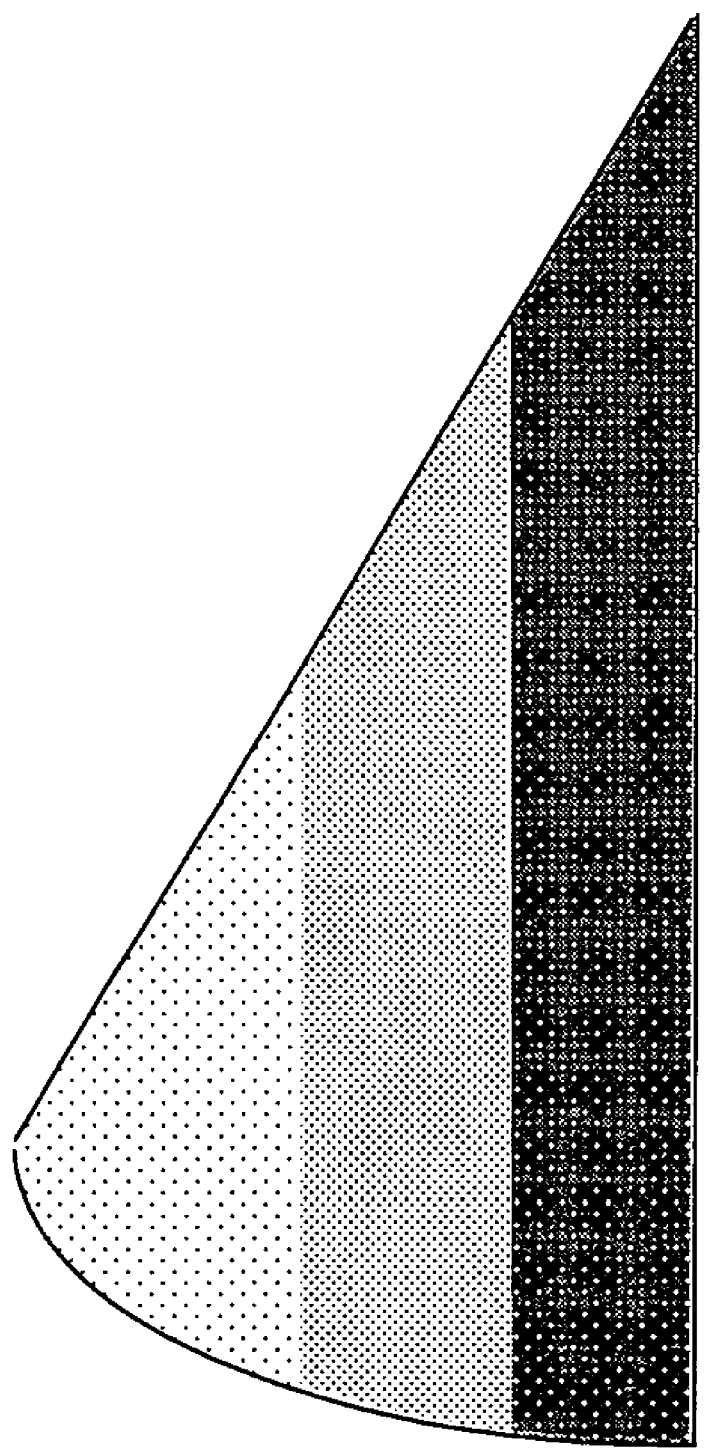
FIG. 3 is a cross-sectional side view of an anatomically-shaped breast prosthesis made according to a further aspect of the present invention.

Now turning to FIG. 3, another embodiment of a prosthesis of the present invention is shown comprising an anatomically-shaped implantable shell or envelope and a gel filler, wherein the gel is formed with greater cohesiveness at the base (i.e. posterior portion) of the implant, decreasing towards the apex or maximum projection (i.e. anterior portion) of the implant.

Figure 4:
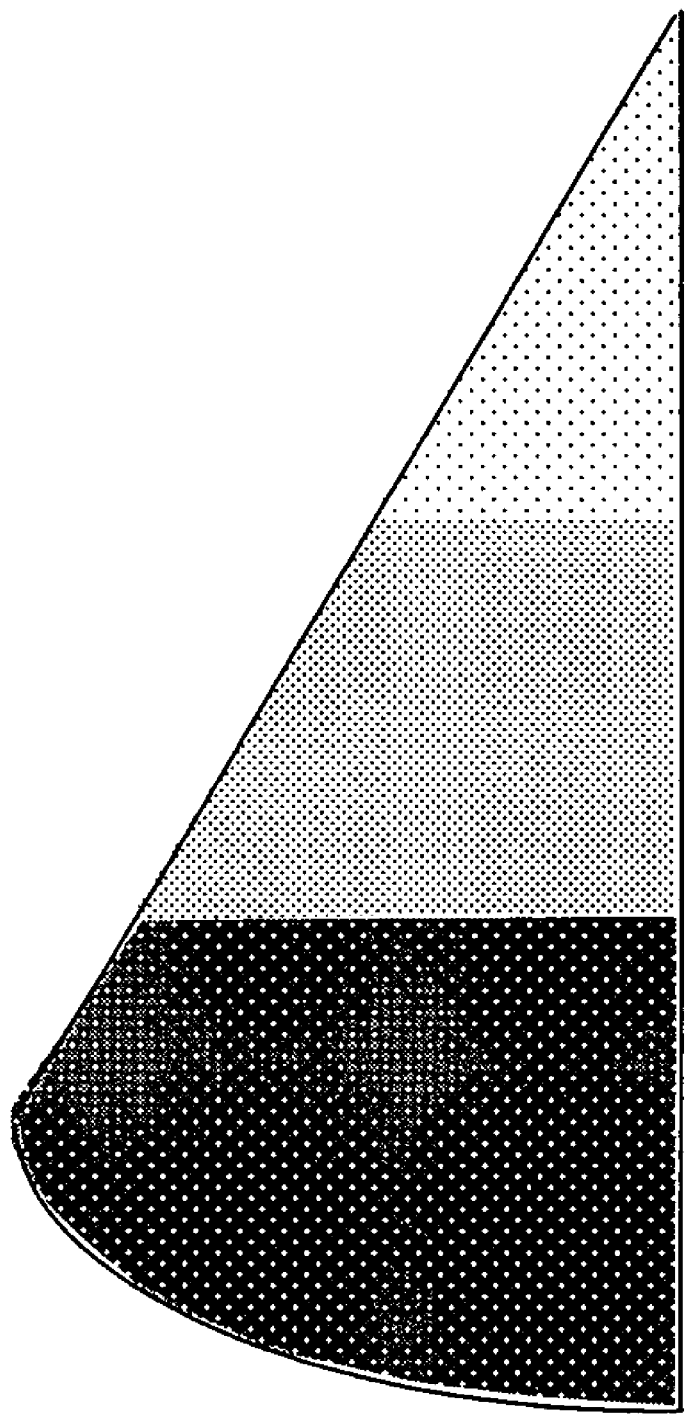
FIG. 4 is a cross-sectional side view of another anatomically-shaped breast prosthesis made according to the present invention.

FIG. 4 shows a further embodiment of a prosthesis of the present invention comprising an anatomically-shaped implantable shell or envelope and a gel filler, wherein the gel is formed with greater cohesiveness at the inferior aspect of the implant, decreasing in horizontal layers towards the superior aspect of the implant.

Figure 5:
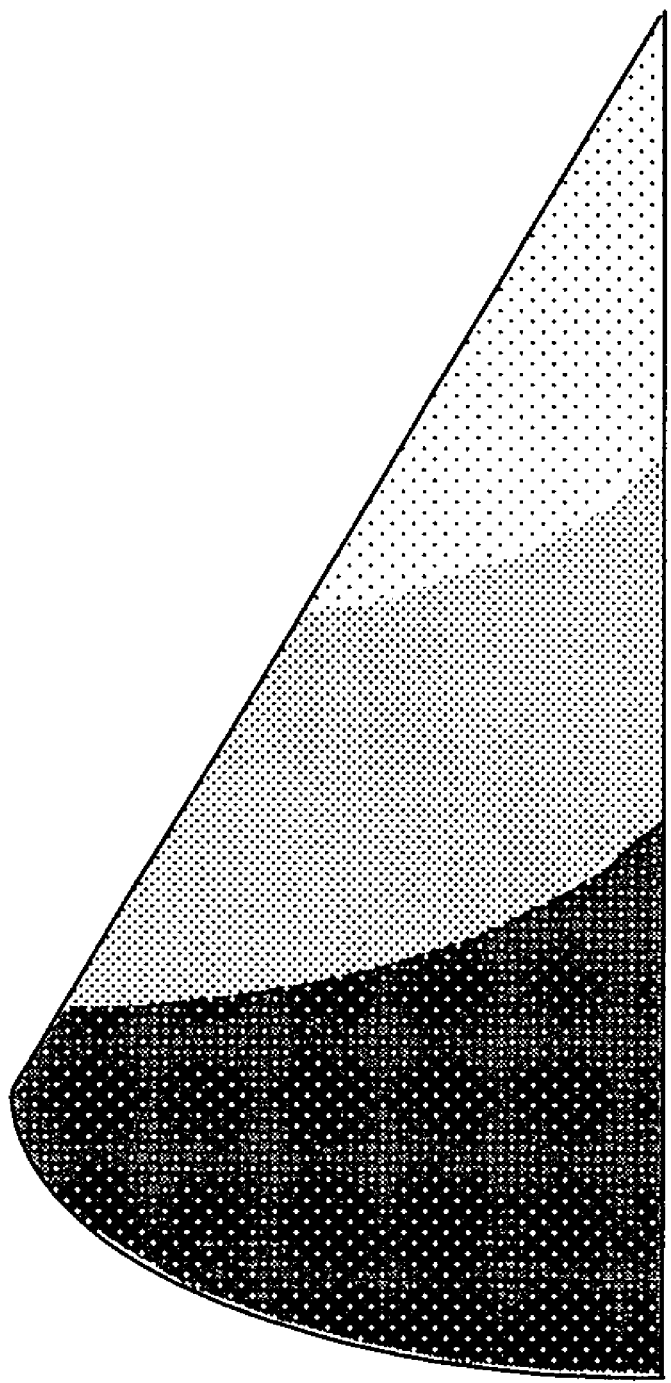
FIG. 5 is a cross-sectional side view of yet another anatomically-shaped breast prosthesis made according to the present invention.

FIG. 5 illustrates yet another embodiment of a prosthesis of the present invention comprising an anatomically-shaped implantable shell or envelope and a gel filler, wherein the gel is formed with greater cohesiveness at the inferior aspect of the implant, decreasing in oblique layers towards the superior aspect of the implant.

It will be apparent to those skilled in the art that various modifications and variations can be made in the present invention and specific examples provided herein without departing from the spirit or scope of the invention. Thus, it is intended that the present invention covers the modifications and variations of this invention that come with the scope of any claims and their equivalents.

What is claimed is:

1. A form-stable breast implant comprising:
   an elastomeric shell, suitable for implantation in a human breast; and
   a plurality of cohesive gel fillers, contained in the elastomeric shell, having at least two different degrees of gel cohesiveness and forming a posterior portion of the implant defining a base and an anterior portion of the implant defining an apex;
   wherein the gel cohesiveness decreases in gradient of vertical layers from the posterior portion toward the anterior portion of the implant.

2. The form-stable implant of claim 1, wherein the gel cohesiveness is greatest at the posterior portion of the implant.

3. The form-stable implant of claim 1, wherein the implant is a mammary implant.

4. The form-stable implant of claim 1, wherein the implant is a soft tissue expander.

5. The form-stable implant of claim 1, wherein the elastomeric shell is textured.

6. The form-stable implant of claim 1, where the implant is anatomically shaped.

7. The form-stable implant of claim 1 further comprising at least one inner lumen.

8. The form-stable implant of claim 1 wherein the different degrees of cohesiveness are defined by different degrees of chemical cross-linking of the gel fillers.

* * * * *